United States Patent [19]

Sheldon et al.

[11] Patent Number: 4,705,513
[45] Date of Patent: Nov. 10, 1987

[54] DISPOSABLE DIAPER WITH WETNESS INDICATOR

[76] Inventors: Sidney Sheldon, 10250 Sunset Blvd., Los Angeles, Calif. 90077; James L. Butler, Jr., 4469 Matilija, Sherman Oaks, Calif. 91423

[21] Appl. No.: 879,459

[22] Filed: Jun. 27, 1986

[51] Int. Cl.⁴ .............................................. A61F 13/16
[52] U.S. Cl. .................................................... 604/361
[58] Field of Search ........................................ 604/361

[56] References Cited

U.S. PATENT DOCUMENTS

| | | | |
|---|---|---|---|
| 3,759,261 | 9/1973 | Wang | 604/361 |
| 4,022,211 | 5/1977 | Timmons et al. | 604/361 |
| 4,192,311 | 3/1980 | Felfoldi | 604/361 |
| 4,231,370 | 11/1980 | Mroz et al. | 604/361 |
| 4,327,731 | 5/1982 | Powell | 604/361 |

Primary Examiner—John D. Yasko
Attorney, Agent, or Firm—Keith D. Beecher

[57] ABSTRACT

A disposable diaper which is capable of providing a readily visible indication when wet which includes a strip of moisture absorbing paper of a selected water insoluble color, or carrying a water insoluble printed pattern on its inner side, the strip being inserted between the absorbent pad of the diaper and the translucent moisture-impervious outer layer. So long as the diaper is dry, the pattern is covered by the carrier strip, and is not visible. However, when the diaper is wet, the carrier strip absorbs the moisture and becomes transparent, so that the pattern is visible through the translucent outer layer not only that the diaper is wet, but the degree of wetness.

4 Claims, 3 Drawing Figures

DISPOSABLE DIAPER WITH WETNESS INDICATOR

BACKGROUND OF THE INVENTION

The disposable diaper of the present invention is of the same general type as disclosed in U.S. Pat. No. 3,759,261—Wang. However, the construction of the present invention is significantly simple as compared with the Wang construction.

It is known that adults sometimes have difficulty in determining whether or not a diaper on a baby is wet or dry without disturbing the baby, and without soiling the hands of the adult. Accordingly the diaper of the present invention is most desirable, since it is capable of readily providing a visible signal when the diaper is wet, and the degree of witness, thereby indicating whether the baby is in need of being changed.

Accordingly, an important objective of the present invention is to provide a disposable diaper having an exceedingly simple means for providing a readily visible indication when the diaper is wet, so that person can determine at a glance whether or not the diaper needs to be changed without disturbing the baby or soiling his or her hands.

The diaper of the present invention possesses the outward appearance of a conventional disposable diaper when dry. However, it displays a readily visible color or pattern when wet.

In accordance with the invention, a carrier layer of absorbent paper, or similar material is provided of a particular color or on which a pattern is formed, and which is placed adjacent to the inner layer of the usual present-day disposable diaper, with the colored surface or pattern facing the inner layer and covered by the carrier. The color or pattern itself is formed of non-soluble ink, or other appropriate non-soluble material.

The inner layer and the carrier are covered by the usual translucent moisture impervious outer layer of the diaper, so that the carrier is sandwiched between the absorbent inner layer and the translucent outer layer.

Whenever the diaper is wet, the color or pattern on the carrier becomes visible through the translucent layer of the diaper, as the carrier absorbs the moisture and becomes transparent.

BRIEF DESCRIPTION OF THE ILLUSTRATED EMBODIMENT

DETAILED DESCRIPTION OF THE DRAWINGS

Figure 1:
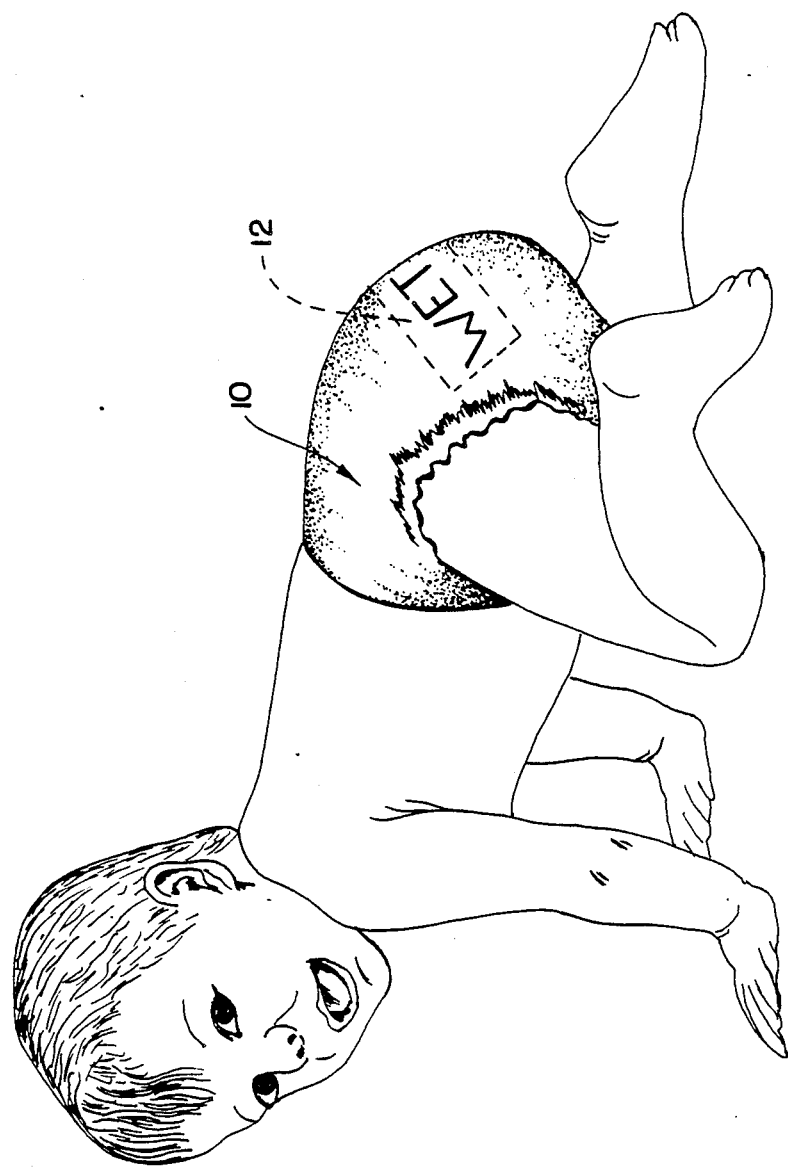
FIG. 1 is a representation of a baby wearing a diaper embodying the concept of the invention and indicating that the diaper is wet.
Figure 2:
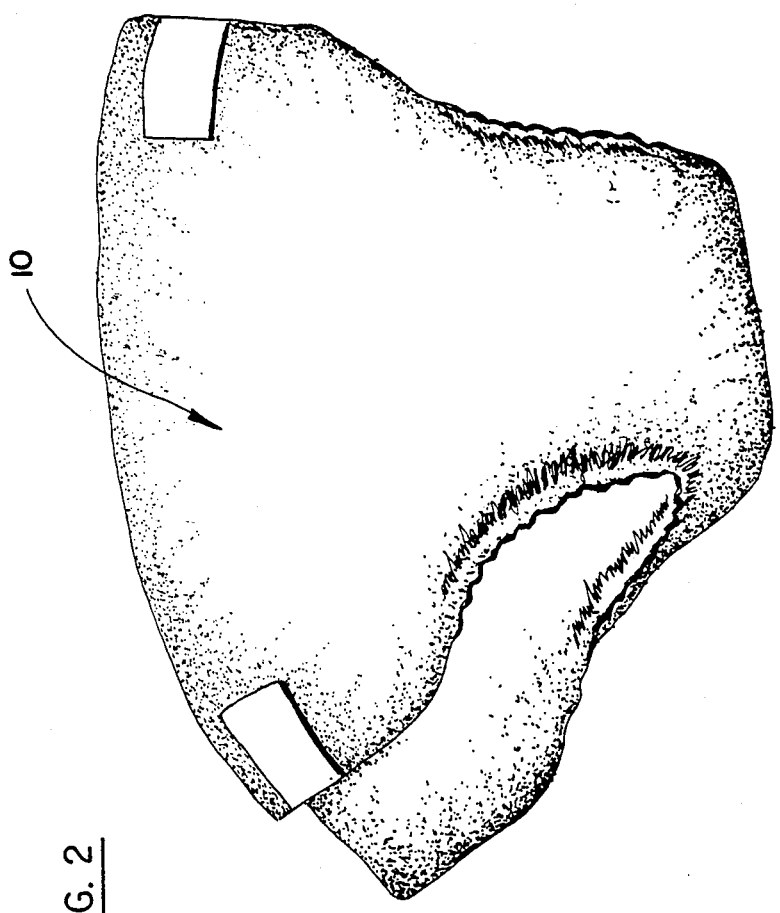
FIG. 2 is a perspective representation of the diaper of FIG. 1.

A usual present-day disposable diaper is designated 10 in FIGS. 1 and 2, and, as mentioned above, the diaper is formed of the usual inner absorbent layer and outer translucent moisture impervious layer.

Figure 3:
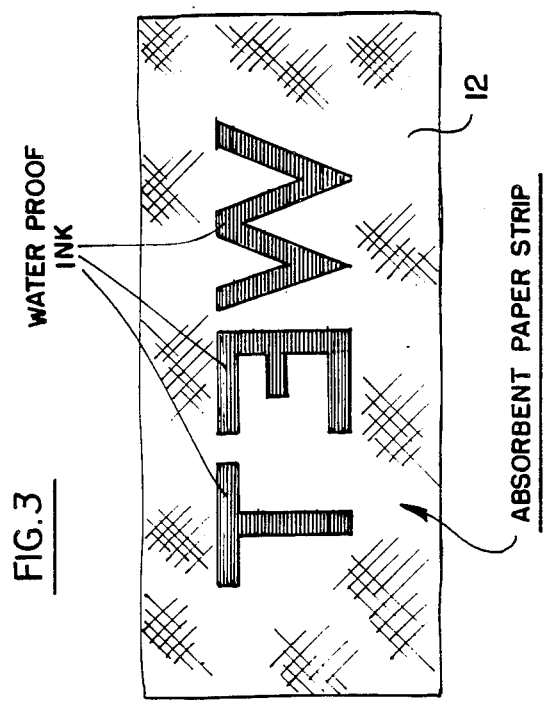
FIG. 3 is a representation of the carrier strip which is incorporated into the diaper in accordance with the concept of the invention.

In accordance with the invention, a strip 12 of, for example, absorbent paper (FIG. 3) is interposed between the outer translucent layer and the inner absorbent layer of disposable diaper 10 with, for example, the word "wet" formed thereon in a mirror image facing inwardly towards the absorbent layer of the diaper.

Accordingly, so long as the diaper is dry, it has the appearance of the normal commercial disposable diaper of FIG. 2. However, when the diaper becomes wet, the absorbent carrier strip 12 absorbs the moisture and becomes transparent, so that the pattern is visible through the carrier layer and through the moisture impervious translucent outer layer, as shown in FIG. 1. Any other appropriate pattern, of course, may be used. The color, word or pattern is formed of water-insoluble ink or paint, or other appropriate substance.

It will be appreciated that while a particular embodiment of the invention has been shown and described, modifications may be made. It is intended in the claims to cover all modifications which come within the true spirit and scope of the invention.

We claim:

1. A diaper assembly capable of providing a visible indication when wet, said diaper assembly comprising an absorbent layer; and a flat strip of absorbent material mounted in said diaper assembly adjacent to the outer surface of said absorbent layer, said flat strip being opaque when dry and essentially transparent when wet, and said flat strip having an insoluble coating imprinted on the surface thereof facing the absorbent layer, said coating being normally shielded by said flat strip and becoming visible through said flat strip when said flat strip absorbs moisture and becomes essentially transparent.

2. The diaper assembly defined in claim 1 and which includes a moisture impervious translucent outer layer, and in which said flat strip of absorbent material is interposed between the absorbent layer and the moisture impervious outer layer, and in which the indicator coating becomes visible through the outer translucent layer when the flat strip absorbs moisture and becomes essentially transparent.

3. The diaper assembly defined in claim 1, in which said flat strip is formed of absorbent paper.

4. The diaper assembly defined in claim 1, in which said insoluble indicator coating is formed of an insoluble ink.

* * * * *